United States Patent
Morille et al.

(10) Patent No.: US 9,629,811 B2
(45) Date of Patent: Apr. 25, 2017

(54) MICROSPHERE COMPOSITIONS, PREPARATION METHOD AND APPLICATIONS THEREOF

(71) Applicant: INSERM (Institut National de la Sante et de la Recherche Medicale), Paris (FR)

(72) Inventors: Marie Morille, Montpellier (FR); Van-Thanh Tran, Ho Chi Minh (VN); Xavier Garric, Montpellier (FR); Jean Coudane, Montpellier (FR); Marie-Claire Venier-Julienne, Angers (FR); Claudia Montero-Menei, Angers (FR)

(73) Assignee: Institut National de la Sante et de la Recherche Medicale (INSERM), Paris (FR)

( * ) Notice: Subject to any disclaimer, the term of this patent is extended or adjusted under 35 U.S.C. 154(b) by 27 days.

(21) Appl. No.: 14/389,211

(22) PCT Filed: Mar. 29, 2013

(86) PCT No.: PCT/EP2013/056813
§ 371 (c)(1),
(2) Date: Sep. 29, 2014

(87) PCT Pub. No.: WO2013/144341
PCT Pub. Date: Oct. 3, 2013

(65) Prior Publication Data
US 2015/0056290 A1   Feb. 26, 2015

(30) Foreign Application Priority Data
Mar. 30, 2012  (EP) .................................... 12305388

(51) Int. Cl.
*A61K 9/50*    (2006.01)
*A61K 9/48*    (2006.01)
(Continued)

(52) U.S. Cl.
CPC ................ *A61K 9/50* (2013.01); *A61K 9/167* (2013.01); *A61K 9/1647* (2013.01);
(Continued)

(58) Field of Classification Search
CPC ........ A61K 9/50; A61K 9/4866; A61K 38/16; A61K 9/5052; A61K 9/5089; A61K 35/00; A61K 9/1647; A61K 9/167
See application file for complete search history.

(56) References Cited

U.S. PATENT DOCUMENTS

2008/0248122 A1* 10/2008 Rashba-Step ........ A61K 9/1647
424/490

FOREIGN PATENT DOCUMENTS

WO       03/092657       11/2003

OTHER PUBLICATIONS

Delcroix et al., "The therapeutic potential of human multipotent mesenchymal stromal cells combined with pharmacologically active microcarriers transplanted in hemi-parkinsonian rats," Biomaterials, 32(6):1560-1573 (2011).
(Continued)

*Primary Examiner* — Trevor Love
(74) *Attorney, Agent, or Firm* — Whitham, Curtis & Cook, P.C.

(57) ABSTRACT

A cell carrying microsphere composition, wherein the microsphere composition comprises a microspheric core comprising a triblock copolymer matrix A-B-A wherein A is selected from poly(lactide-co-glycolide) (PLGA) or polylactide (PLA) and B is poloxamer or poloxamine, wherein the microspheric core is coated with a cell adhesion coating
(Continued)

and further comprises whole cells or cell fragments bonded to the cell adhesion coating, a process for the preparation of a cell carrying microsphere composition, and applications thereof.

11 Claims, 6 Drawing Sheets

(51) Int. Cl.
  *A61K 38/16* (2006.01)
  *A61K 35/00* (2006.01)
  *A61K 9/16* (2006.01)
(52) U.S. Cl.
  CPC .......... *A61K 9/4866* (2013.01); *A61K 9/5052* (2013.01); *A61K 9/5089* (2013.01); *A61K 35/00* (2013.01); *A61K 38/16* (2013.01)

(56) References Cited

OTHER PUBLICATIONS

Garbayo et al., "Neuroprotective properties of marrow-isolated adult multilineage-inducible cells in rat hippocampus following global cerebral ischemia are enhanced when complexed to biomimetic microcarriers," J. Neurochem., 119 (5):972-988 (2011).

International Search Report in PCT/EP2013/056813 dated May 15, 2013.

Tatard et al., "In vivo evaluation of pharmacologically active microcarriers releasing nerve growth factor and conveying PC12 cells," Cell Transplant., 13(5):573-583 (2004).

Tatard et al., "Pharmacologically active microcarriers releasing glial cell line—derived neurotrophic factor: Survival and differentiation of embryonic dopaminergic neurons after grafting in hemiparkinsonian rats," Biomaterials, 28(11):1978-1988 (2007).

Tatard et al., "Pharmacologically active microcarriers: a tool for cell therapy," Biomaterials, 26(17):3727-3737 (2005).

Tran et al., "Protein-loaded PLGAPEGPLGA microspheres: A tool for cell therapy," Eur. J. Pharm., 45(1):128-137 (2011) XP028341137.

Morille, et al., 'New PLGA-P188-PLGA matrix enhances TGF-β3 release from pharmacologically active microcarriers and promotes chondrogenesis of mesenchymal stem cells,' J. of Controlled Release, 2013, 170: 99-110.

* cited by examiner

MICROSPHERE COMPOSITIONS, PREPARATION METHOD AND APPLICATIONS THEREOF

The present application is filed pursuant to 35 U.S.C. 371 as a U.S. National Phase application of International Patent Application No. PCT/EP2013/056813, which was filed Mar. 29, 2013, claiming the benefit of priority to European Patent Application No. 12305388.6, which was filed on Mar. 30, 2012. The entire text of the aforementioned applications is incorporated herein by reference in its entirety.

FIELD OF THE INVENTION

The present invention relates to a cell carrying microsphere composition, its preparation method and applications thereof.

BACKGROUND OF THE INVENTION

WO03092657 relates to microparticles which are based on a biocompatible and biodegradable material. The surface thereof comprises cells of interest or fragments of same and in further comprise molecules of at least one active substance on the aforementioned cells or the environment thereof during the implantation of the microparticles, said molecules being released by the microparticles in a prolonged and controlled manner.

Cell therapy by grafting autologous or non-autologous precursor or mature cells is a promising strategy to repair diseased organs. Moreover, the recent development of stem cell biology has provided further excitement for cell-based therapy. Several teams have used embryonic stem cells, adult stem cells, tissue-derived stem cells or more recently induced pluripotent stem cells to repair injured tissues. In this context, adult stem cells and particularly mesenchymal stem cells (MSCs), also named multipotent mesenchymal stromal cells, appear as an attractive cell source for tissue engineering because of their safety, their relative accessibility from different tissues and the possibility of performing autografts. Indeed, these stem cells have been successfully used for musculoskeletal tissue engineering and regeneration applications due to their intrinsic property to differentiate. They are also able to differentiate into other cell lineages, such as neuron-like cells or endothelial-like cells, under specific conditions. Moreover, mesenchymal stem cells are known to be able to migrate to injured tissues and some of their reparative properties are mediated by paracrine mechanisms including their immunomodulatory actions. However, after transplantation the majority of the cells die or if previously induced toward a differentiated phenotype do not maintain this induced phenotype. Consequently due to the small cell number and a non-desired modification of its behavior the tissue repair process is not efficient and the cells do not integrate correctly the host environment. For an efficient use in therapy, cell engraftment needs to be ameliorated, that is particularly the short but also long-term survival and functional state of the cells after transplantation.

Growth and differentiating factors may improve survival and differentiation of the cells, and may also affect the immediate environment, thus allowing better graft integration. Various growth factors, cytokines or morphogens have been widely used for directing the differentiation of MSCs. Nevertheless, the administration of these factors still remains a technological challenge, due to their short half-life, pleiotropic actions and their limited passage through biological barriers. Therefore, the use of delivery carriers for these factors, such as nano or microdevices is now a crucial choice to both protect and allow a controlled and sustained release of for example a protein.

In addition to cytokines, several parameters including composition of extracellular matrix (ECM) and three-dimensionality of the microenvironment have been shown to strongly influence the survival and differentiation of human mesenchymal stem cells. In this regard, scaffolds providing the ECM surface have been developed for example for brain neuronal repair (Delcroix et al Biomaterials 2011).

Within this context, an attractive strategy is to provide these associated parameters within an implantable small-sized pharmacologically active scaffold conveying stem cells, thus stimulating transplanted stem cell engraftment by providing an appropriate microenvironment to the cells in vivo.

The present inventors directed their investigations to pharmacologically active microcarriers (Coated microspheres), which are biocompatible and biodegradable microspheres, engineered to preferably continuously release an active molecule and which present a cell adhesion surface of extracellular matrix molecules or cell adhesion molecules supplying a three-dimensional structure for the transported cells. These parameters combined in one small-sized microcarrier act on the transported cells and on the surrounding tissue. The proof of concept of this unique and simple device delivering cells and proteins has first been validated for neuroprotection and tissue repair for the treatment of neurological disorders using a neuronal cell line, neuronal precursors and adult stem cells combined to Coated microspheres with different cell adhesion surfaces (laminin, fibronectin, poly-D-lysine) and/or growth factors (NGF, GDNF, NT-3) (Tatard et al 2004, Tatard et al 2007, Delcroix et al 2011, Garbayo et al 2011). Furthermore, with the goal to provide an efficient support for cartilage repair, pharmacologically active microcarriers releasing transforming growth factor 3 (TGF-β3) associated to human mesenchymal stem cells were shown to induce their chondrogenic differentiation in vitro and in vivo [Bouffi C, et al. The role of pharmacologically active microcarriers releasing TGF-β3 in cartilage formation in vivo by mesenchymal stem cells. Biomaterials. 2010; 31:6485-931]. Nevertheless, these poly (D,L lactide-co-glycolide) (PLGA) pharmacologically active microcarriers released TGF-β3 in a low and incomplete manner (25% of bioactive protein in 30 days) due to protein-polymer interaction during the release period, leading to protein instability. Interactions are enhanced by the necessity of working at low encapsulation loadings in order to accurately deliver these highly active therapeutic proteins at physiological levels. In an attempt to circumvent this problem, hydrophilic segments poly(ethylene glycol) (PEG) were introduced into hydrophobic polyesters, like PLGA, forming triblock copolymer microspheres. The presence of PEG segments increase water uptake and therefore a higher protein release (TRAN et al. European Journal of Pharmaceutical Sciences 45 (2012) 128-137).

It is an object of the present invention to eliminate or at least to substantially mitigate said drawbacks of existing products and methods.

SUMMARY OF THE INVENTION

Now the applicant has discovered that the number of whole cells or cell fragments carried by coated microsphere compositions based on specific triblock copolymers was considerably increased. Additionally the use of the specific triblock copolymers increases whole cell number. Furthermore the nature of the coating may increase the number of whole cells or cell fragments carried by coated microsphere compositions and influence cell differentiation. Additionally, the specific triblock copolymers are capable of embedding an active ingredient, preferably a protein, and provide sustained release matrix compositions with remarkable properties of high active ingredient release. Accordingly, whole cells of interest or fragments thereof linked to said matrix compositions may interact with the active ingredient, and therefore a better efficacy of the whole cells or fragments is obtained.

DESCRIPTION OF THE PREFERRED EMBODIMENTS

A subject of the present application is therefore a cell carrying microsphere composition, wherein the microsphere composition comprises a microspheric core comprising a triblock copolymer matrix A-B-A wherein A is selected from poly(lactide-co-glycolide) (PLGA) or polylactide (PLA) and B is poloxamer or poloxamine, wherein the microspheric core is coated with a cell adhesion coating and further comprises whole cells or cell fragments bonded to the cell adhesion coating.

Preferred triblock copolymer matrices are poly(D,L-lactide-co-glycolide)-poloxamer-poly(D,L-lactide-co-glycolide), poly(D,L-lactide-co-glycolide)-poloxamine-poly(D,L-lactide-co-glycolide)

and poly(lactide)-poloxamer-poly(lactide), particularly poly(D,L-lactide-co-glycolide)-poloxamer-poly(D,L-lactide-co-glycolide).

Microspheres are small, about spherical particles, with diameters in the micrometer range, typically 1 μm to 1000 μm, preferably 5 μm to 500 μm, in particular 10 μm to 250 μm, particularly 25 μm to 150 μm, quite particularly 50 μm to 80 μm.

The A-B-A copolymer, more particularly poly(D,L-lactide-co-glycolide)-poloxamer-poly(D,L-lactide-co-glycolide), is a triblock copolymer.

The preferred first block is poly (D,L-lactide-co-glycolide).

The second preferred block is a poloxamer or poloxamine, preferably a poloxamer. Poloxamers are themselves nonionic triblock copolymers. A poloxamer with a polyoxypropylene mass of between 1,000 and 3,500 g/mol, preferably between 1,000 and 2,000 g/mol and a polyoxyethylene content of between 40 and 90%, preferably between 80 and 85%, is preferred, more particularly poloxamer 188. Poloxamer 188 has an average Molecular Weight of 8,400 and about 80% oxyethylene by weight.

A mixture of triblock copolymers may be used.

The PLGA-poloxamine-PLGA triblock may have a structure of a copolymer block with four PLGA molecules bound to a single poloxamine molecule.

The proportion of poloxamer or poloxamine in the triblock copolymer is between 0.4 and 40% (w/w), preferably between 8 and 20% (w/w).

A poly(D,L-lactide-co-glycolide)-poloxamer-poly(D,L-lactide-co-glycolide) triblock copolymer with a poloxamer molecular mass of between 2,000 and 20,000 g/mol, preferably between 2,000 and 15,000 g/mol, more preferably between 7,000 and 10,000 g/mol and a poloxamer content of between 0.4 and 50%, preferably between 8 and 20%, more preferably between 9 and 12%, is particularly preferred.

The cell carrying microsphere composition of the invention is useful for carrying cells of interest. The cells, i.e. cell fragments or preferably whole cells, more preferably functional whole cells, interact with the microsphere via a cell adhesion surface coating.

According to the invention, the whole cells or cell fragments are indirectly bound to said microsphere compositions. In the present application by "cell adhesion surface coating", is meant a surface comprising or consisting of extracellular matrix molecules or cell adhesion molecules, or fragments of the aforementioned molecules or fragments of molecules, enhancing cell adhesion. This cell adhesion surface coating may also modify cell function particularly proliferation or survival or more particularly differentiation. The microsphere compositions are for this purpose completely coated or partly coated or present a cell adhesion surface obtained by another manner, with compounds enhancing cell adhesion or function (survival or differentiation for example) including those selected from the group consisting of poly-D-lysine (PDL), poly-L-lysine, arginine-glycine-aspartic acid tripeptide (RGD), polyornithine, polyethyleneamine, other synthetic molecules such as fibronectin-like compounds, or extracellular matrix molecules (fibronectin (FN), laminin, collagen) or cell adhesion molecules (N-CAM, selectines) or fragments of extracellular matrix molecules or cell adhesion molecules. A single compound or a mixture of such compounds may be used. Fibronectin-like compounds are commercially available for example from SIGMA.

The cells are bonded to the surface of the cell carrying microspheres by a coating preferably comprising fibronectin and poly-D-lysine, preferably at a 60-40 ratio.

The binding mechanism of whole cells or cell fragments to microspheres may be of different nature. Cell attachment may be obtained by intermolecular forces, for example by ionic forces (cationic poly-D-lysine for example), van der Waals forces or hydrogen bonds. Cell attachment may particularly be obtained via a receptor present on the cell surface, according to a conventional ligand-receptor binding (integrins on the cell surface and extracellular matrix molecules like FN or laminin present on the cell adhesion coating for example or cell adhesion molecules (N-CAM) on the cell surface and N-CAM present on the cell adhesion coating).

Cells, preferably human cells, can be for example adult autologous cells, foetal cells, transformed cell lines or not, stem cells, multipotent or pluripotent cells, reprogrammed cells. These cells can be used in various diseases in regenerative medicine.

This is for example the case of transplantation of hepatocytes and islets of Langerhans for the treatment of diabetes.

In the case of neurotransplantation, a cell may be a PC12 cell line capable of secreting dopamine and differentiate into sympathetic neurons-like under the effect of NGF. Other examples of cells include cells used in cell transplantation for repair of the liver, myocardium, central nervous system, transplantation of islets of Langerhans, bone marrow cells, adult cells, foetal cells, reprogrammed cells, transformed or not transformed cell lines, stem cells, genetically modified cells, cells producing recombinant virus defective for replication, hepatocytes, islet cells, nerve cells, muscle cells, hematopoietic cells, bone cells.

Other suitable cells are cells for gene transfer in vivo, as cells containing a transgene, cells producing recombinant viruses defective for replication that will infect host cells nearby.

By "cell fragment", is meant a pharmacologically active part of a whole cell. Pharmacologically active cell fragments may be obtained from whole cells, for example by sonication which disrupts cell membranes and releases cellular contents or by enzyme-based disruption. Conventional test allow to assess whether the desired pharmacological effect is kept. A same microsphere may comprise whole cells and cell fragments.

A person skilled in the art can easily understand when the term "a" signifies "at least one" or "one or several" in the specification. For example when the text provides that the microspheric core is coated with a cell adhesion coating, "at least one cell adhesion coating" is meant, or when the text provides that the microsphere compositions of the invention comprise an active ingredient within the microspheres, "at least one active ingredient" is meant.

Preferred cell carrying microsphere compositions of the invention comprise an active ingredient embedded within the microspheres. The active ingredient (s) is (are) embedded in a matrix of the copolymer. Therefore the dissolving active ingredient has to find its way out by diffusion through water-filled pores, through the copolymer or by dissolution of the encapsulating copolymer. The core provides a sustained release matrix composition with remarkable properties of high active ingredient release An active ingredient (s) may also be present on the surface of the microsphere.

The active ingredient (preferably a protein) provides the possibility to control in vitro or in vivo proliferation and differentiation of the cells, or modulate their tissue environment (avoiding immunological rejection phenomena, promoting angiogenesis). The active ingredient also provides the possibility to control the effect of cell fragments.

In the case of sustained release microsphere compositions carrying cells of interest, the active ingredient is preferably an active agent which modulates the cells or their effects. As previously mentioned, modulation is preferably proliferation or differentiation, or modification of the tissue environment of these cells.

The active ingredient, preferably a protein, is therefore advantageously an immunomodulatory agent such as cytokines, preferably interleukines or a factor contributing to the survival of the said cells to extend their function over time such as growth factors preferably neurotrophins, the bone morphogenetic protein extended family comprising transforming growth factors, or factors that induce their differentiation like morphogens of protein nature or non protein nature like retinoic acid.

Conversely, the active ingredient may be a toxic molecule transported to the cell, programming and his death and disposal such as Fas ligand.

The protein active ingredients are therefore advantageously an enzyme, a growth factor, a cytokine, a hormone, an antibody, an antibody fragment, a coagulation factor or other protein known for its action on cells or altering their tissue environment.

The protein active ingredients include more particularly growth factors, cytokines, or immunomodulatory factors affecting cell differentiation, including those selected from the group consisting of neurotrophins such as NGF, BNDF, NT-3, etc. . . . the TGFfis GDNF family, the FGF EGF, PDGF, interleukins such as IL-1 IL-2, chemokines, retinoic acid, erythropoietin etc. or mixtures thereof.

The term "protein" active ingredient includes polypeptide and oligopeptide active ingredients.

Preferred active ingredients promote cell survival, function, or direct the differentiation of stem cells to a determined phenotype.

They can also alter the tissue environment by reducing immune responses and graft rejection, or promoting integration by increasing angiogenesis.

Active ingredients used in the present compositions can also be used to control the expression of a gene present in a genetically modified cell, which is under control of a promoter responding to these ingredients, such as growth factors.

Protein active ingredients are preferably used as nanoparticles. They are particularly obtained by nanoprecipitation.

More conventional active ingredients, of non proteic nature, include for example antioxidant molecules (vitamins, flavonoids), drugs for chemotherapy (5-FU, BCNU, docetaxel, paclitaxel . . . ), radiosensitizer drugs such as (5-iodo-2'-deoxyuridine (Idurd . . . ).

A subject of the present invention is also a process for the preparation of a cell carrying microsphere composition defined above comprising the steps consisting in
  providing microspheric cores comprising a triblock copolymer matrix A-B-A wherein A is selected from poly (lactide-co-glycolide) (PLGA) or polylactide (PLA) and B is poloxamer or poloxamine
  fully or partly coating the microspheres with a cell adhesion compound, and
  contacting whole cells or cell fragments with the microspheres presenting the cell adhesion surface
for obtaining a cell carrying microsphere composition comprising whole cells or cell fragments.

Under preferred conditions for implementing the invention, the cell adhesion surface is obtained by chemical surface modification of the polymeric matrix for example by grafting synthetic adhesion peptides such as polylysine or RGD-like peptides such as RGD or peptides of extracellular matrix molecules such as IKVAV or of cell adhesion molecules such as KHIFSDDSSE onto the surface of the microspheres.

A further subject of the present invention is also a process for the preparation of a cell carrying microsphere composition defined above further comprising an active ingredient, preferably a protein, embedded in the triblock copolymer, comprising the steps consisting in
  providing a solution of a A-B-A (preferably poly(D,L-lactide-co-glycolide)-poloxamer-poly(D,L-lactide-co-glycolide)) triblock copolymer in a solvent of polymers, preferably an organic solvent,
  providing an active ingredient, (preferably a protein),
  adding the active ingredient in the solution of the A-B-A triblock copolymer, emulsifying or suspending, preferably suspending the active ingredient in the case of a protein,
  emulsifying the solution of A-B-A triblock copolymer in an aqueous phase containing a surfactant,
  removing the solvent of polymers, whereby microspheres forming a matrix wherein the active ingredient is embedded, are obtained,
  isolating the microspheres,
  fully or partly coating the microspheres thus obtained with a cell adhesion compound, and
  contacting whole cells or cell fragments with the microspheres presenting a cell adhesion surface for obtaining a sustained release microsphere composition comprising whole cells or cell fragments.

Under other preferred conditions for implementing the above processes of the invention, the coating step may be implemented by mixing the cell adhesion compounds of the coating with the microspheres in suspension at appropriate proportions. Coating is preferably obtained by adsorption of the adhesion compound(s) onto the microspheres.

Under still other preferred conditions for implementing the above processes of the invention, the attachment step can be performed by mixing the cell suspension with the coated microsphere suspension in appropriate proportions.

A sustained release microsphere composition comprising an active ingredient, preferably a protein, wherein the active ingredient is embedded in a coated A-B-A (preferably poly (D,L-lactide-co-glycolide)-poloxamer-poly(D,L-lactide-co-glycolide)) matrix and further comprising whole cells or cell fragments is thus obtained.

The microspheres may be fully coated or partly coated, or present a cell adhesion surface obtained by another manner with compounds enhancing cell adhesion or cell function (survival for example) or both.

The solvent may be any suitable solvent of the triblock copolymer and preferably an organic solvent, particularly a mixture of methylene chloride and acetone or glycofurol which is an injectable solvent.

A proteic active ingredient is preferably previously obtained by nanoprecipitation. Therefore, interaction between the copolymer and the protein is reduced. The protein does not need to be stabilized by additives such as albumin.

Removal of an organic solvent is for example obtained by addition of an extractive medium, preferably water.

The microspheres thus obtained are preferably isolated by physical separation such as filtration.

Furthermore, the isolated microspheres are preferably lyophilized.

Because of the specific triblock copolymer used, the cell carrying microsphere composition comprising at least one active ingredient according to the invention has advantageous properties.

The specific triblock copolymer used provides the composition with interesting amount of bound whole cells or cell fragments as shown hereafter.

The use of the specific triblock copolymers also increases whole cell number.

Furthermore the nature of the coating may increase the number of whole cells or cell fragments carried by coated microsphere compositions and may influence cell differentiation.

Additionally, the specific triblock copolymers are capable of embedding an active ingredient, preferably a protein, and provide sustained release matrix compositions with remarkable properties of controlled release profile and additionally high active ingredient release. Accordingly, whole cells of interest or fragments thereof linked to said matrix compositions may interact with the active ingredient, and therefore a better efficacy of the whole cells or fragments is obtained.

The triblock copolymers of microspheres are biocompatible and capable of being resorbed into the human body.

The above cell carrying microsphere compositions may be used for the preparation of a composition, wherein said microspheres are provided on their surface with whole cells of interest or fragments thereof and also optionally include at least one ingredient active on said cells or their environment, and/or an active ingredient being released from the microparticles according to a sustained and controlled release.

This is why a further object of the present invention is a coated cell carrying microsphere composition as defined above provided with whole cells of interest or fragments thereof for use in a method for therapeutic treatment of the human or animal body.

A further object of the present invention is a coated cell carrying microsphere composition wherein said microspheres are provided on their surface with whole cells of interest or fragments thereof and further include an ingredient active vis-à-vis said whole cells or fragments or their environment as defined above, for use in a method for therapeutic treatment of the human or animal body.

More specifically, a further object of the present invention is a cell carrying microsphere composition wherein said microspheres are provided on their surface with whole cells of interest or fragments thereof and also include an ingredient active vis-à-vis said whole cells or fragments or their environment as defined above for use in a method for therapeutic treatment of degenerative diseases, preferably neurodegenerative diseases (Parkinson, Huntington, Alzheimer . . . ), spinal cord injury, osteo-articular diseases (osteoarthritis, post-traumatic osteoarthritis), ischemic diseases (cerebral ischemia, erection malfunctions, urinary incontinence, peripheral limb ischemia), kidney malfunction.

In view of their therapeutic use, the above compositions are preferably formulated as pharmaceutical compositions.

The present invention therefore includes pharmaceutical compositions comprising a cell carrying microsphere composition of the present invention, together with a pharmaceutically acceptable carrier, and optionally other therapeutic and/or prophylactic ingredient(s).

In general, the cell carrying microsphere compositions of the present invention will be administered in a therapeutically effective amount by any of the accepted modes of administration for agents used for similar utilities. Suitable dosage ranges depend upon several factors such as the severity of the disease to be treated, the age and relative health of the subject, the potency of the active ingredient or cell or fragment used, the route and form of administration, and the indication towards which the administration is directed. One of ordinary skill in the art of treating such diseases will be able, without undue experimentation and in reliance upon personal knowledge and the disclosure of this application, to ascertain a therapeutically effective amount of the compounds of the present invention for a given disease.

The cell carrying microsphere compositions of the present invention will usually be administered as pharmaceutical formulations including those suitable for parenteral administration.

The cell carrying microsphere compositions of the present invention, together with one or more conventional adjuvants, carriers, or diluents may be placed into the form of pharmaceutical compositions and unit dosages. The pharmaceutical compositions and unit dosage forms may comprise conventional ingredients in conventional proportions, with or without additional active compounds or ingredients, and the unit dosage forms may contain any suitable effective amount of the active ingredients commensurate with the intended daily dosage range to be employed.

The cell carrying microsphere compositions may particularly be employed in the form of sterile injectable preparation for parenteral uses.

For parenteral or local administration (e.g., by injection, preferably bolus injection or stereotaxic injection), the cell carrying microsphere compositions of the present invention may be formulated and may be presented in unit dose form in ampoules, bottle, pre-filled syringes small volume infusion or in multi-dose containers with or without formulatory or additive agent.

The compositions may take such forms as suspensions in oily or aqueous vehicles. Examples of non-aqueous or oily diluents solvents or vehicles include propylene glycol, polyethylene glycol, vegetable oils (e.g., olive oil, and injectable organic esters (e.g., ethyl oleate), and may contain formulatory agents such as preserving, wetting, emulsifying or suspending, stabilizing and/or dispersing agents. Alternatively, the cell carrying microsphere compositions may be in powder form, obtained by aseptic isolation of sterile solid or by lyophilization from solution for constitution before use with a suitable vehicle, e.g., sterile, pyrogen-free water.

Preferred conditions for implementing the cell carrying microsphere compositions described above also apply to the other subjects of the invention envisaged above, particularly the cell carrying microsphere compositions provided with cells, the above processes and pharmaceutical formulations. For example in all the cases, the active ingredient used is preferably a protein.

Figure 1:
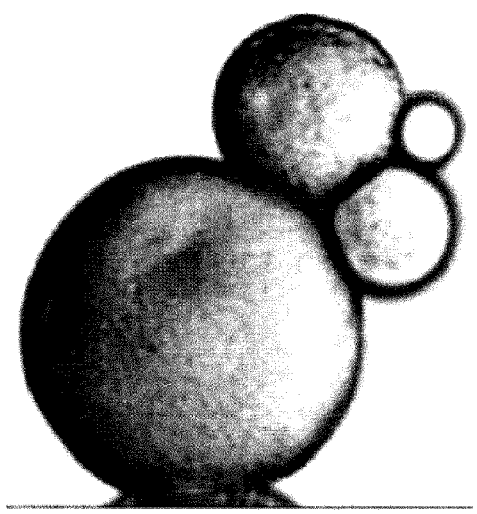
FIG. 1 shows unloaded microspheres with their coating.

The scope of the invention can be understood better by referring to the examples given below, the aim of which is to explain the advantages of the invention.

Preparation 1: Preparation of PLGA-P188-PLGA, PLA-P188-PLA, and PLGA-Poloxamine-PLGA Copolymers The triblock copolymer PLGA-P188-PLGA (ABA copolymer) was prepared by ring-opening polymerisation of DL-lactide and glycolide using Poloxamer 188 as an initiator, and stannous octoate [Sn(Oct)2] as a catalyst.

Various precise amounts of poloxamer 188 (1, 2, 3) or poloxamine (4) and of poly (lactide-co-glycolide) (PLGA) (1, 2, 4) or PLA (3) were mixed and introduced into 100 mL round-bottom flasks with stannous octoate [Sn(Oct)2] according to Table 1.

TABLE 1

| Components used for copolymer synthesis. | | | | |
|---|---|---|---|---|
| Polymer | 1 | 2 | 3 | 4 |
| poloxamer 188 | 5 g | 4.8 g | 2.4 g | 0 |
| Poloxamine Tetronic 1107 | 0 | 0 | 0 | 2.1 g |
| lactide | 26.4 g | 25 g | 22.6 g | 12.7 g |
| glycolide | 21.2 g | 20 g | 0 g | 10.2 g |
| stannous octoate | 48 mg | 46 mg | 23 mg | 23 mg |
| Polymer | 5 | 6 | 7 | 8 | 9 |
| poloxamer 188 | 3.47 g | 5.92 g | 0 | 0 | 0 |
| Poloxamine Tetronic 1107 | 0 | 0 | 2.1 g | 3.16 g | 5.45 g |
| lactide | 9.15 g | 7.8 g | 12.7 g | 9.33 g | 8.06 g |
| glycolide | 7.37 g | 6.28 g | 10.2 g | 7.51 g | 6.49 |
| stannous octoate | 33 mg | 57 mg | 23 mg | 34 mg | 23 mg |

The mixtures of Table 1 were heated to 140° C. and degassed by 15 vacuum-nitrogen purge cycles in order to remove moisture and oxygen. Flasks were then frozen at 0° C. and sealed under dynamic reduced pressure at $10^{-3}$ mbar. Polymerisation was allowed to proceed at 140° C. under constant agitation. After 5 days, the products were recovered by dissolution in 500 mL methylene chloride and then precipitated by adding the same volume of ethanol.

Finally, the triblock copolymer was filtered, washed with cold ethanol and dried overnight at 45° C. under reduced pressure, up to constant weight.

Analysis

The PLGA-P188-PLGA and other copolymers were characterised by 1H NMR and Size Exclusion Chromatography (SEC). The molecular weight of the PLGA block was determined by using the integration ratio of resonance of PEG units at 3.6 ppm and PLGA blocks at 4.76 ppm in the 1H NMR spectra. The molecular weights of the copolymers were determined by SEC using Waters Inc. equipment fitted with a PIgel 5 µm mixed-C (60 cm) column as the stationary phase and a Waters 410 refractometric detector, eluted with DMF at 1 mL·min$^{-1}$. Typically, samples were dissolved in DMF at 10 mg/mL and filtered on PTFE filter Millex®-FH (pore size 0.45 µm) from Millipore Corporation, prior to 20 µL of the solution of copolymer being injected. The Mn and Mw were expressed according to calibration against poly(styrene) standards.

Results

Calculated by $^1$H NMR

TABLE 2

| Code name | Actual molecular weight | | |
|---|---|---|---|
| | Poloxamer segment Mn (kDa) | PLGA or PLA segment Mn (kDa) | Mn total (kDa) |
| PLGA-P188-PLGA (polymer 1) | 8.4 | 40.7 | 89.8 |
| PLA-P188-PLA (polymer 3) | 8.4 | 32.7 | 73.7 |
| PLGA-P188-PLGA (polymer 5) | 8.4 | 17.3 | 43 |
| PLGA-P188-PLGA (polymer 6) | 8.4 | 9.8 | 28 |
| PLGA-T1107-PLGA (polymer 7) | 15 | 30.0 | 135 |
| PLGA-T1107-PLGA (polymer 8) | 15 | 17.3 | 84.2 |
| PLGA-T1107-PLGA (polymer 9) | 15 | 6.7 | 41.8 |

Calculated by Size Exclusion Chromatography

TABLE 3

| Code name | Actual molecular weight | | |
|---|---|---|---|
| | Mn total (kDa) | Mw total (kDa) | Ip |
| PLGA-P188-PLGA (copolymer 1) | 60.6 | 96.7 | 1.6 |
| PLA-P188-PLA (copolymer 3) | 40.24 | 60.1 | 1.5 |
| PLGA-P188-PLGA (copolymer 5) | 51.8 | 73.0 | 1.41 |
| PLGA-P188-PLGA (copolymer 6) | 41.4 | 56.7 | 1.37 |
| PLGA-T1107-PLGA (copolymer 7) | 47.0 | 67.7 | 1.44 |
| PLGA-T1107-PLGA (copolymer 8) | 48.4 | 65.3 | 1.35 |
| PLGA-T1107-PLGA (copolymer 9) | 59.6 | 71.5 | 1.2 |

The polymers used as references are uncapped (free carboxylic acid group at the terminal end) PLGA 37.5/25 (Mn 14,000 Da) provided by Phusis (Saint-Ismier, France) and PLGA-PEG-PLGA (Mn 45,300 for PLGA segment, Mn 4,000 for PEG segment) provided by Institut des biomolécules Max Mousseron, CNRS UMR 5247, Montpellier, F-34093 France.

Preparation 2: Preparation of Nanoprecipitated Lysozyme Coupled with Poloxamer 188 (1-10 Ratio)

General Procedure for Preparation of Protein Nanoparticles:

The protein was nano-precipitated using a process previously described by Bouffi C et al. http://www.sciencedirect-.com/science/article/pii/S0142961210013487-bib55: The role of pharmacologically active microcarriers releasing TGF-β3 in cartilage formation in vivo by mesenchymal stem cells. Biomaterials. 2010; 31:6485-93 and Giteau A et al. Reversible protein precipitation to ensure stability during encapsulation within PLGA microspheres. European Journal of Pharmaceutics and Biopharmaceutics. 2008; 70:127-36.

45 µl of a solution containing 900 µg of lysozyme and 9 mg of poloxamer 188 in NaCl 0.3 M are added to glycofurol (1.04 g) to form a 1 mL suspension at room temperature. The complex particles are recovered by centrifugation (10,000 g, 30 min, 4° C.) and elimination of the supernatant. To prepare the 100 mg microsphere batch, 600 µg of lysozyme and 6 mg of poloxamer 188 were used.

Preparation 3: Preparation of Nanoprecipitated Lysozyme Coupled with Poloxamer 188 (3A 1-10 Ratio; 3B 1-20 Ratio)

10 µL of NaCl 0.3M solution containing 150 µg of lysozyme and various amounts of poloxamer 188 depending of the lysozyme-additive ratio (1.5 mg or 3 mg P188 for 1-10 or 1-20 ratio respectively) were added to 1.1 g glycofurol. The complex particles are recovered by centrifugation (10,000 g, 30 min, 4° C.) and elimination of the supernatant.

Preparation 4: Preparation of Nanoprecipitated TGF-β3 Coupled with Poloxamer 188 (4A: 1-10 Ratio; 4B: 1-20 Ratio)

The general procedure was adapted to lyophilized TGF-β3.

10 µl of a TRIS-HCl 0.75M, NaCl 2M (pH=7.4) solution containing 50 µg of TGF-β3 and various amounts of poloxamer 188 (P188, Lutrol® F68, BASF, Levallois-Perret, France) depending of the TGF-β3-poloxamer 188 ratio (0.5 or 1 mg P188 for 1-10 and 1-20 ratio respectively) was added to 1.077 g of cold glycofurol (4° C.) (Sigma-Aldrich, St Quentin Fallavier, France). The complex particles are recovered by centrifugation (10,000 g, 30 min, 4° C.) and elimination of the supernatant.

Preparation 5: Preparation of Nanoprecipitated Human Serum Albumin (HSA) Coupled with Poloxamer 188 (5A: 1-10 Ratio; 5B: 1-20 Ratio)

Nanoprecipitated HSA with either a 1-10 or 1-20 protein-poloxamer 188 ratio was produced in a similar manner as preparation 4 and as previously described (Delcroix et al. Biomaterials 2011). 10 µL of NaCl 0.3 M containing 750 µg of HSA and various amounts of poloxamer 188 depending of the HSA-additive ratio (7.5 mg or 15 mg P188 for 1-10 or 1-20 ratio respectively) were added to 1.1 g glycofurol. The complex particles are recovered by centrifugation (10,000 g, 30 min, 4° C.) and elimination of the supernatant.

Preparation 6: Preparation of Human Serum Albumin (HSA) Coupled with Poloxamer 188 Nanoparticles (6A: 1-10 Ratio; 6B: 1-20 Ratio)

Nanoprecipitated HSA with either a 1-10 or 1-20 protein-poloxamer 188 ratio was produced in a similar manner as preparation 5 and as previously described (Delcroix et al. Biomaterials 2011). 10 µl of NaCl 0.3 M containing 250 µg of HSA and various amounts of poloxamer 188 depending of the HSA-additif ratio (2.5 or 5 mg P188 for 1-10 or 1-20 ratio respectively) were added to 1.1 g glycofurol. The complex particles are recovered by centrifugation (10,000 g, 30 min, 4° C.) and elimination of the supernatant.

Preparation 7: Preparation of Human Mesenchymal Stem Cells (MSC)

Human MSC cultures were established from bone marrow aspirates from patients undergoing hip replacement surgery, after informed consent, as previously described [Bouffi et al Biomaterials 2010]. Briefly, cell suspensions were plated in a complete α-minimum essential medium (αMEM) (Lonza, Levallois-Perret, France) supplemented with 10% foetal bovine serum (FBS) (Hyclone, ThermoFisherScientific), 2 mM glutamine, 100 U/ml penicillin, 100 mg/ml streptomycin (Lonza) and 1 ng/ml human basic fibroblast growth factor (bFGF) (R&D Systems, Lille, France). MSCs were shown to be positive for CD44, CD73, CD90 and CD105 and negative for CD14, CD34 and CD45 and used between passages 3 and 4.

Preparation 8: Polymer Films

Polymer films of copolymer 1 and PLGA were prepared by solvent casting; 10 mg of copolymer (copolymer 1 or PLGA) were dissolved in DMSO, poured onto a glass dish and subsequently air-dried. Films of copolymer 1 and films of PLGA were obtained.

Preparation 9: Reference Microspheres

Reference Microspheres without lysozyme were produced following the process of preparation 12 hereafter, and were named unloaded-MS. In this case, the organic solution contained 2 mL of organic solvent (3:1 methylene chloride/acetone) and 150 mg of copolymer.

Preparation 10: Preparation of Coated Microspheres

To obtain unloaded microspheres, polymer microspheres (preparation 9 or preparation 13) were coated with fibronectin (FN) (Sigma-Aldrich, St Quentin Fallavier, France) and poly-D-Lysine (PDL) (Sigma-Aldrich, St Quentin Fallavier, France).

Coating solutions were prepared in Dulbecco's Phosphate-Buffered Saline DPBS (LONZA, Levallois-Perret, France). The concentration of the coating molecules (15 µg/mL) was 6 µg/mL of FN and 9 µg/mL of PDL (corresponding to a 60:40 ratio of FN:PDL).

5 mg of microspheres were resuspended in DPBS and sonicated until full dispersion of the microspheres. The solution containing the FN and PDL cell adhesion molecules was mixed to the microsphere suspension (final volume: 10 mL) and placed under rotation at 15 rpm at 37° C. during 1 h30. After coating, coated microspheres were washed 3 times in distilled sterile water, lyophilized and finally kept at −20° C. for long-term storage. Every tube was covered with Sigmacote® (Sigma-Aldrich, St Quentin Fallavier, France) to prevent product loss on the tube walls.

Preparation 11: Preparation of Lysozyme/Poloxamer 188 Particles Embedded in Copolymer 1, Copolymer 3, and PLGA Microspheres (Microsphere Batch 150 Mg), and Copolymer 5, Copolymer 6, Copolymer 7, Copolymer 8, Copolymer 9 (Microsphere Batch 100 Mg)

General procedure for embedding protein active ingredients in microspheres:

The encapsulation of protein active ingredients was performed as described by TRAN et al. Protein-loaded PLGA-PEG-PLGA microspheres: A tool for cell therapy, European Journal of Pharmaceutical Sciences 45 (2012) 128-137

Lysozyme coupled with poloxamer 188 nanoparticles (1-10 ratio) of preparation 2 was carefully dispersed in an organic solution (2 mL; 3:1 methylene chloride:acetone) containing 150 mg of copolymers 1 or 3 of preparation 1 or PLGA (reference polymer) (batch 100 mg:1.34 mL 3:1 methylene chloride:acetone containing 100 mg of copolymers 5, 6, 7, 8 or 9 of preparation 1). This organic suspension was emulsified in a poly(vinyl alcohol) aqueous solution (90 mL, 4% w/v) or (batch 100 mg:60 mL, 4% w/v) maintained at room temperature and mechanically stirred at 550 rpm for 1 min. (Heidolph RZR 2041, Merck Eurolab, Paris, France). After the addition of 100 mL of deionised water and stirring for 10 min., 500 mL of deionised water (batch 100 mg: 66 mL and 334 mL of deionised water respectively) was added to the resulting o/w emulsion and stirred at 300 rpm for 20 min. to extract the organic solvent. The suspension was sieved through a 125 µm stainless mesh and then recovered by sieving through a polypropylene 37 µm filter. Microspheres were washed with 500 mL of deionised water and then freeze-dried before storage at −20° C.

Protein loading was of 6 µg of lysozyme (Sigma-Aldrich, St Quentin Fallavier, France)/mg of PLGA-P188-PLGA microspheres, PLA-P188-PLA microspheres, PLGA-T1107-PLGA microspheres or PLGA microspheres.

Analysis

The average volume diameter and the size distribution of the microspheres obtained were evaluated using a Multisizer™ Coulter Counter (Beckman Coulter, Roissy, France).

Differential scanning calorimetry (DSC) was performed with a Mettler Toledo Star System (Mettler-Toledo, Viroflay, France). Samples (10 mg) were placed in a sealed aluminium crucible; they were first heated from 25 to 80° C., then thermograms covering a range from _50 to 100° C. were recorded at a heating rate of 10° C. min$^{-1}$. The Tg of the polymer were determined thanks to the DSC technique.

TABLE 4

Characterization of lysozyme/poloxamer 188 (1:10) loaded microspheres.

| Polymer | Tg (° C.) | Mean size ± SD (µm) | Encapsulation yield (%) |
|---|---|---|---|
| PLGA (reference) See end of preparation 1 | 26 | 51 ± 28 | 60 ± 7 |
| PLGA-P188-PLGA (copolymer 1) | 17 | 63 ± 23 | 64 ± 5 |
| PLA-P188-PLA | 29 | 67 ± 23 | 66 ± 5 |

TABLE 4-continued

Characterization of lysozyme/poloxamer 188 (1:10) loaded microspheres.

| Polymer | Tg (° C.) | Mean size ± SD (μm) | Encapsulation yield (%) |
|---|---|---|---|
| (copolymer 3) | | Batch 100 mg | |
| PLGA-P188-PLGA (copolymer 5) | 13 | 80 ± 21 | 90 |
| PLGA-P188-PLGA (copolymer 6) | 2 | 85 ± 23 | 85 |
| PLGA-T1107-PLGA (copolymer 7) | 39 | 70 ± 20 | 80 |
| PLGA-T1107-PLGA (copolymer 8) | −1 | 84 ± 20 | — |
| PLGA-T1107-PLGA (copolymer 9) | −10 | 87 ± 17 | 42 |

Preparation 12: Preparation of Lysozyme/Poloxamer 188 Particles Embedded in PLGA-P188-PLGA Microspheres (Copolymer 2) and PLGA (Microsphere Batch 150 Mg)

Nanoprecipitated proteins of preparations 3 and 5 were harvested by centrifugation and were dispersed in an organic solution (2 mL; 3:1 methylene chloride/acetone) containing 150 mg of copolymer. The organic solution was emulsified in a poly-(vinyl alcohol) aqueous solution (90 mL, 4% w/v) maintained at 1° C. and mechanically stirred for 1 min (550 rpm) (Heidolph RZR 2041, Merck Eurolab, Paris, France). After the addition of 100 mL of deionised water and stirring for 10 min, the resulting o/w emulsion was added to deionised water (500 mL) and stirred at 550 rpm for a further 20 min to extract the organic solvent. Finally, the formed microparticles were filtered on a 5 μm filter (HVLP type, Millipore SA, Guyancourt, France), washed with 500 mL of deionised water and freeze-dried before storage at +4° C.

Preparation 13: Microencapsulation of TGF-β3/Poloxamer 188 and HSA/Poloxamer 188 Particles in PLGA-P188-PLGA Microspheres (Copolymer 2 and PLGA) (Microsphere Batch 50 mg)

The procedure for embedding TGF-β3/poloxamer 188 particles and HSA/poloxamer 188 particles in PLGA-P188-PLGA and PLGA microspheres was the same as in Preparation 12, the microsphere batch in this case is 50 mg.

TGF-β3 and HSA were nano-precipitated separately using the processes described in preparation 4 and 6 respectively.

The nanoprecipitated TGF-β3 and HSA was harvested by centrifugation and were dispersed in the organic phase (670 μL of 50 mg PLGA-P188-PLGA (polymer 2) or PLGA dissolved in a 3:1 methylene chloride:acetone solution), which was emulsified in a poly(vinylalcohol) (Mowiol® 4-88, Kuraray Specialities Europe, Frankfurt, Germany) aqueous solution (30 ml, 4% w/v at 1° C.) and mechanically stirred at 550 rpm for 1 min (Heidolph, RZR 2041, Merck Eurolab, Paris, France). After addition of 33 ml of deionized water and stirring for 10 min, the emulsion was added to 167 mL deionized water and stirred for 20 min to extract the organic solvent. Finally, the microspheres were filtered on a 0.45 μm filter (HVLP type, Millipore SA, Guyancourt, France), washed and freeze-dried.

Protein loading was of 1 μg for TGF-β3 (Peprotech, Paris, France) together with 5 μg of human serum albumin ((Sigma-Aldrich, St Quentin Fallavier, France)/mg of PLGA-P188-PLGA and PLGA microspheres.

Example 1

Preparation of FN and PDL Coated Unloaded PLGA-P188-PLGA Microspheres with Bonded Human Mesenchymal Stem Cells Step 1: Preparation of FN and PDL Coated Microspheres PLGA-P188-PLGA (copolymer 2) microspheres were coated with fibronectin (FN) (Sigma-Aldrich, St Quentin Fallavier, France) and poly-D-Lysine (PDL) (Sigma-Aldrich, St Quentin Fallavier, France) (preparation 10).

Coating solutions were prepared in Dulbecco's Phosphate-Buffered Saline DPBS (LONZA, Levallois-Perret, France). The concentration of the coating molecules (15 μg/mL) was 6 μg/mL of FN and 9 μg/mL of PDL (corresponding to a 60:40 ratio of FN:PDL).

5 mg of PLGA-P188-PLGA (copolymer 2) microspheres were resuspended in DPBS and sonicated until full dispersion of the microspheres. The solution containing the FN and PDL coating molecules was mixed to the microsphere suspension (final volume: 10 mL) and placed under rotation at 15 rpm at 37° C. during 1 h30. After coating, microspheres were washed 3 times in distilled sterile water, lyophilized and finally kept at −20° C. for long-term storage. Each and every tube was covered with Sigmacote® (Sigma-Aldrich, St Quentin Fallavier, France) to prevent product loss on the tube walls.

Immunofluorescence staining using an anti-fibronectin antibody shows the FN coating of the microspheres. Interferential Nomarsky microscopy and superposition of Nomarsky and fluorescent images of PLGA-P188-PLGA microspheres of this example. This coating is satisfactory and FN covers all the surface of the Coated microspheres as shown in FIG. 1.

Step 2: Preparation of FN and PDL Coated Microspheres with Bonded Human Mesenchymal Stem Cells Human Mesenchymal Stem Cells of preparation 7 were washed with PBS, detached with 0.16% trypsin (Sigma), 0.02% EDTA (Lonza) solution, and pelleted at 1400 rpm for 10 min.

Cell pellets were resuspended in culture medium supplemented with 3% FBS. 0.75 mg lyophilized FN and PDL coated microsphere composition of preparation 10 were resuspended in coated Eppendorf tubes (Sigmacote®, Sigma) containing α-MEM medium, 3% FBS for 15 min. The suspension of FN and PDL coated microsphere composition of step 1 was sonicated and briefly vortexed prior to addition of the cell suspension ($0.25 \times 10^6$ cells/0.5 mg microsphere compositions). The mixture was then gently flushed and plated in 1.9 $cm^2$ Costar ultra-low cluster plate (#3473, Corning, Avon, France). Plates were incubated at 37° C. during 4 h to allow cell attachment on FN and PDL coated microspheres surface. This suspension culture of microsphere compositions/cell aggregates or complexes were recovered, washed with α-MEM and pelleted by centrifugation at 200 g for 2 min.

Samples were prepared for scanning electron microscopy analysis as previously described [Tatard et al 2007 Biomaterials)]. Briefly, unloaded coated microspheres (preparation 10) were washed in PBS, fixed with glutaraldehyde 1% and with osmium 1% and then dehydrated with alcohol. Afterwards, they were soaked in hexamethyldisylasane, were covered by a thick layer of carbon and finally observed.

Cell adhesion to the surface of unloaded coated microspheres (Preparation 10) was assessed using light microscopy (A) and scanning electron microscopy (B). Pictures obtained are reported on FIG. 2.

Figure 2:
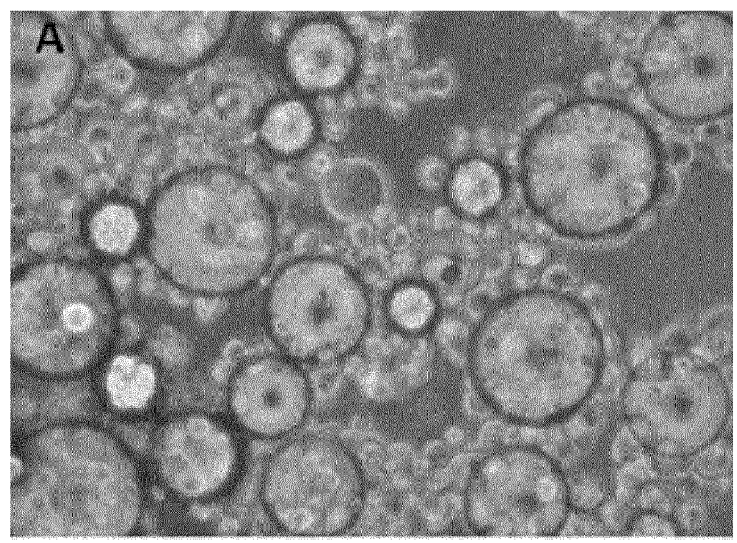
FIG. 2 shows cell adhesion to the surface of unloaded coated microspheres (Preparation 10) assessed using light microscopy (A) and scanning electron microscopy (B).
Figure 2:
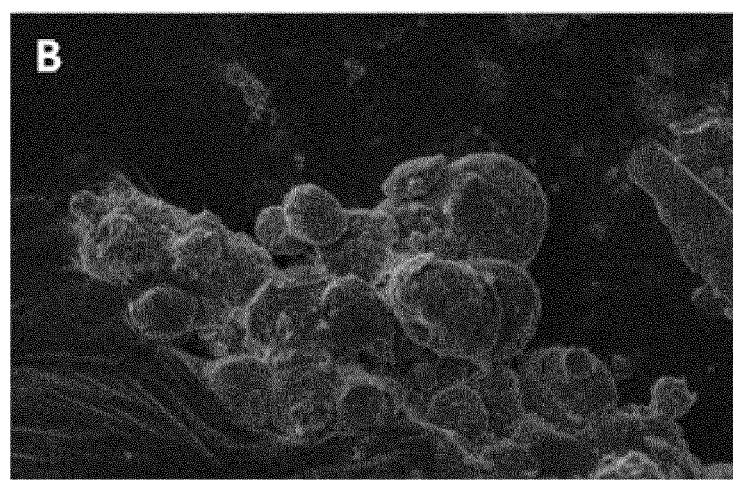

FIG. 2 shows hMSC/unloaded coated micropsheres (PLGA-P188-PLGA)/cell complexes by light microscopy. These cells formed 3D complexes with the coated microspheres as observed by scanning electron microscopy Example 2

Preparation of FN and PDL Coated Microspheres Containing Embedded TGF-33/HSA with Bonded Human Mesenchymal Stem Cells Step 1: Preparation of FN and PDL Coated Microspheres The coating of microspheres of preparation 13 was performed in the same manner as that described in example 1 step 1. The same results were obtained.

Step 2: Preparation of FN and PDL Coated Microspheres with Bonded Human Mesenchymal Stem Cells The cells were bonded to these microspheres in exactly the same manner as that described in example 1 step 2. The same results were obtained.

Similar preparations of coated unloaded triblock copolymers microspheres with bonded Human Mesenchymal Stem Cells, and of corresponding microspheres with bonded Human Mesenchymal Stem Cells were manufactured, using triblock copolymers 6-9.

Methods and Results of Analysis

1—Cell Adhesion Coating on Polymeric Film

Films of polymers (preparation 8) were incubated in a 10 µg/mL solution of FN for 1.5 h at 37° C. The coated polymer films were washed three times with PBS.

The FN coating was determined by immunofluorescence. Briefly, a saturation step with a PBS solution containing 4% BSA for 60 min at room temperature was performed. Polymer films were washed three times with PBS, followed by incubation with a monoclonal mouse, antihuman, fibronectin antibody (1:100) overnight at 4° C. The sections were then washed with PBS and incubated with a biotinylated horse, anti-mouse, IgG antibody (1:200) for 60 min, washed in PBS and incubated with Streptavidin-fluoprobe 547 (1:500) for 40 min Isotype control was also performed.

Figure 3:
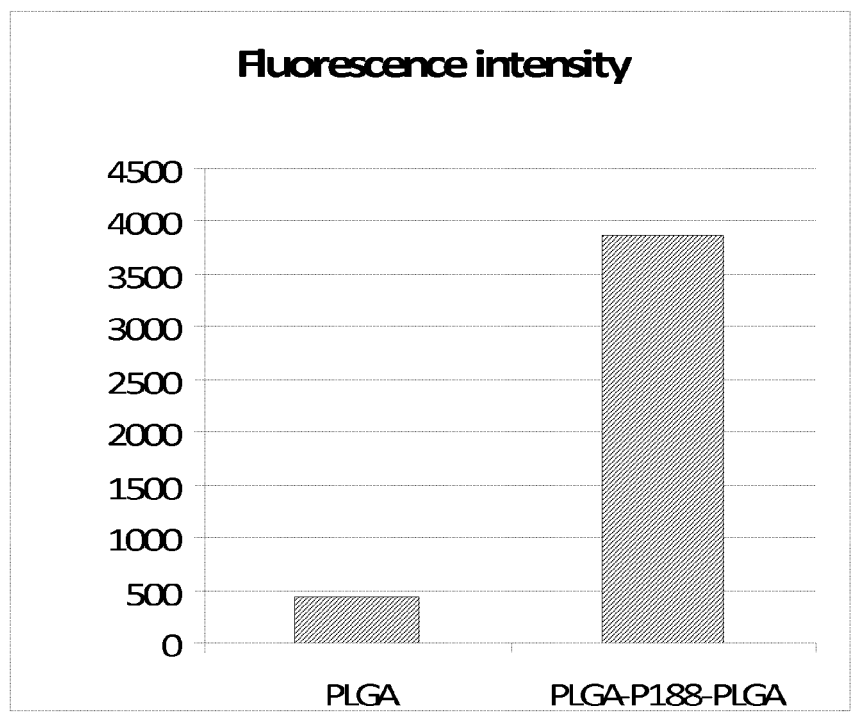
FIG. 3 shows the semi-quantitative fluorescence intensity of the fibronectin cell adhesion surface on the triblock co-polymers (polymeric film) compared to PLGA.

FIG. 3 shows the semi-quantitative fluorescence intensity of the fibronectin cell adhesion surface on the triblock co-polymers (polymeric film) compared to PLGA.

High fluorescence intensity indicates high fibronectin adsorption on the polymer films studied, and therefore a good fibronectin coating. The fluorescence intensity is higher on PLGA-P188-PLGA copolymer compared to PLGA, that means a better coating with fibronectine.

2. Analysis of Coating of Unloaded Microspheres

The zeta potential of the microspheres was determined using a Malvern Zetasizer® (Nano Series DTS 1060, Malvern Instruments S.A., Worcestershire, UK). The measure of zeta potential was achieved on microsphere suspension (0.3 mg/mL in NaCl 1 mM) thanks to the conversion of electrophoretic mobility values to ζ-potentials using Smoluchowski's equation. Results are presented as mean±standard deviation.

PLGA and PLGA-poloxamer-PLGA microspheres showed positive zeta potentials values with the FN cell adhesion surface that evolved from −8.1±2.3 mV to +7.9±0.8 mV for the PLGA-P188-PLGA microspheres. These results show that the microspheres are well coated, this coating is satisfactory for cell adhesion since a positively charged cell adhesion surface promotes adhesion of the cells.

3. Formation of Cell-Unloaded Coated Microspheres Complexes (Example 1, Polymer 2, Polymer Reference) and Cell-Microsphere Complexes (Preparation 9+Preparation 7, Polymer 2)

hMSCs were washed with PBS, detached with 0.16% trypsin 0.02% EDTA solution (Lonza, Levallois-Perret, France) and pelleted at 1400 rpm for 10 min. Cell pellets were resuspended in culture medium supplemented with 3% FBS. 0.75 mg lyophilized microspheres (preparation 9 or 10) were resuspended in coated Eppendorf tubes (Sigmacote, Sigma) containing α-MEM medium, 3% FBS for 15 min. coated microsphere suspension was sonicated and briefly vortexed prior to addition of the cell suspension ($0.25 \times 10^6$ cells/0.5 mg coated microspheres). The mixture was then gently flushed and plated in 1.9 cm$^2$ Costar ultra-low cluster plate (#3473, Corning, Avon, France).

Figure 4:
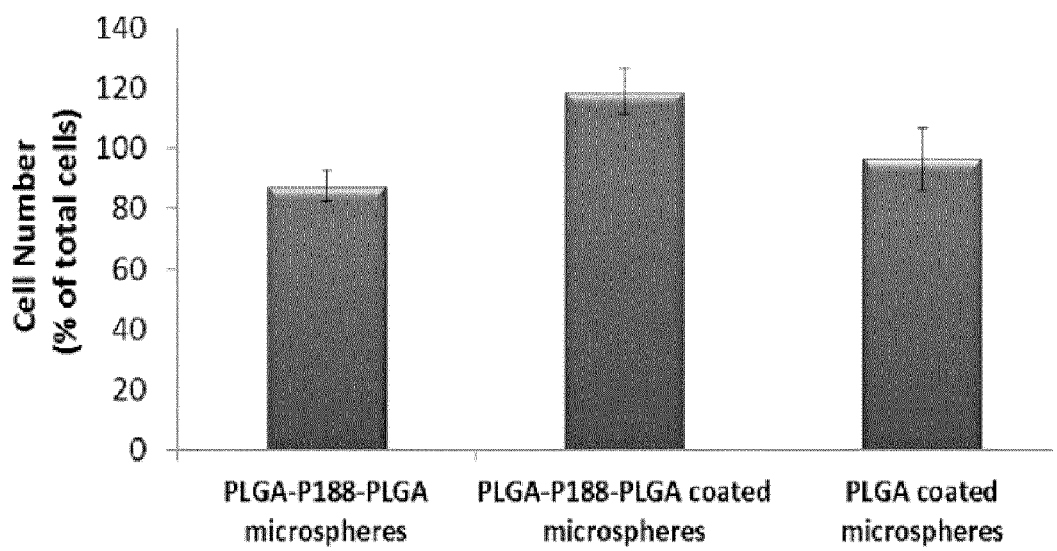
FIG. 4 is a graph illustrating the number of hMSC adhered onto PLGA-P188-PLGA microspheres, PLGA or PLGA-P188-PLGA coated microspheres (microspheres with fibronectin/PDL cell adhesion surface) 4 h after incubation.

Cell adherence was estimated at 4 h by Cyquant assay revealing the number of viable cells, The results are shown on FIG. 4: cell adherence at 4 hours onto microspheres of PLGA-P188-PLGA (preparation 9, polymer 2), Unloaded coated microspheres of PLGA (preparation 10, polymer ref) and unloaded coated microspheres of PLGA-P188-PLGA (preparation 10, polymer 2).

The coating increases the cell adherence, the cell adherence is 118% of the total cells for unloaded coated microspheres compare to 86% for the same non coated microspheres. Moreover, the cell adherence is better with coated PLGA-P188-PLGA microspheres compared to reference polymer PLGA, 120% and 97% respectively.

Figure 5:
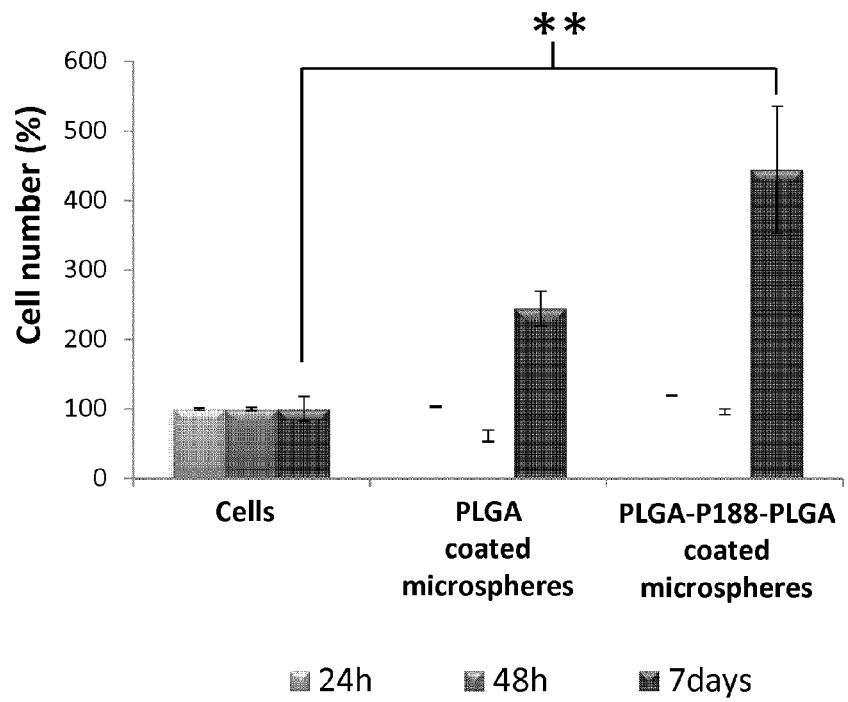
FIG. 5 shows the number of hMSC on coated microspheres formulated with PLGA or PLGA-P188-PLGA as a function of time.

4. Cell Proliferation/Survival on Unloaded Coated Microspheres (Preparation 10)

hMSCs were washed with PBS, detached with 0.16% trypsin 0.02% EDTA solution (Lonza, Levallois-Perret, France) and pelleted at 1400 rpm for 10 min. Cell pellets were resuspended in culture medium supplemented with 3% FBS. 0.75 mg lyophilized coated microspheres were resuspended in coated Eppendorf tubes (Sigmacote®, Sigma) containing α-MEM medium, 3% FBS for 15 min. Coated microsphere suspension was sonicated and briefly vortexed prior to addition of the cell suspension ($0.25 \times 10^6$ cells/0.5 mg coated microspheres). The mixture was then gently flushed and plated in 1.9 cm2 Costar ultra-low cluster plate (#3473, Corning, Avon, France). This suspension culture was maintained over time and cell viability was estimated at various time intervals (24 h, 48 h and 7 days) and live cells adhered to coated microspheres were quantified using the Cyquant Cell Proliferation Assay® (Invitrogen, France) following the manufacturer's guidelines. The results are shown on FIG. 5. The stars ** indicate significant difference ($p<0.01$), n=3.

After 24 h, 48 h, and even 7 days after cell attachment, the cell/coated microsphere complexes were maintained and no dead cells were observed throughout the follow up. After 7 days of cell culture, the hMSCs alone did not proliferate, whereas those forming complexes with the two kinds of coated microspheres proliferated, resulting in a significantly increased cell number. In addition, the proliferation assay showed that the number of cells particularly increased when hMSCs were cultured with unloaded PLGA-P188-PLGA coated microspheres.

Thus the number of cells on the coated PLGA-P188-PLGA microspheres is increased significantly at day 7 suggesting that these coated microspheres stimulated cell proliferation or/and survival over time.

5. Amount of Encapsulated Active Lysozyme and In Vitro Evaluation of Active Lysozyme Release (Preparation 11)

To detect any loss in biological activity during the encapsulation process, the amount of active protein extracted from microspheres of example 1 was determined after dissolution of the microspheres in DMSO.

Lysozyme loaded microspheres (10 mg, 3 batches) were dissolved in 0.9 mL DMSO in a 5 mL PTFE tube. After 1 h, 3 mL of 0.01 M HCl were added. The solution was left to stand for one further hour.

The amount of active lysozyme was determined by measuring the turbidity change in a *M. lysodeikticus* bacterial cell suspension as previously reported A Aubert-Pouessel et al. in vitro delivery system for assessing the biological integrity of protein upon release from PLGA microspheres. Pharm Res. 2002; 19:1046-51. Hundred microliter of a lysozyme solution was added to 2.9 mL of a 0.015% w/v *M. lysodeikticus* suspension in TRIS-HCl (0.01 M, pH 7.4) buffer solution. After incubation (37° C., 4 h), the absorbance was measured at 450 nm. The amount of active protein was calculated with the aid of a standard curve.

The results of encapsulation yield are reported in table 4. The encapsulation yield is between 60 and 66% depending of the polymer, which means that the protein is properly embedded into the polymer matrix.

Protein In Vitro Release
a) Lysozyme—Preparation 11

The in vitro release profile of lysozyme from microspheres (preparation 11) was determined by adding 500 µL of 0.05M TRIS-HCl buffer, pH 7.4, containing 0.1% w/v BSA and 0.09% w/v NaCl to 10 mg of microspheres, into the centrifugation tubes. The tubes were closed and incubated in a shaken water bath (37° C., 125 rpm). At determined intervals, the tubes were centrifuged for 5 min. at 2,800 g to collect the supernatant and to analyse the pH and lysozyme and poloxamer release. The supernatant was then replaced by fresh buffer.

Figure 6:
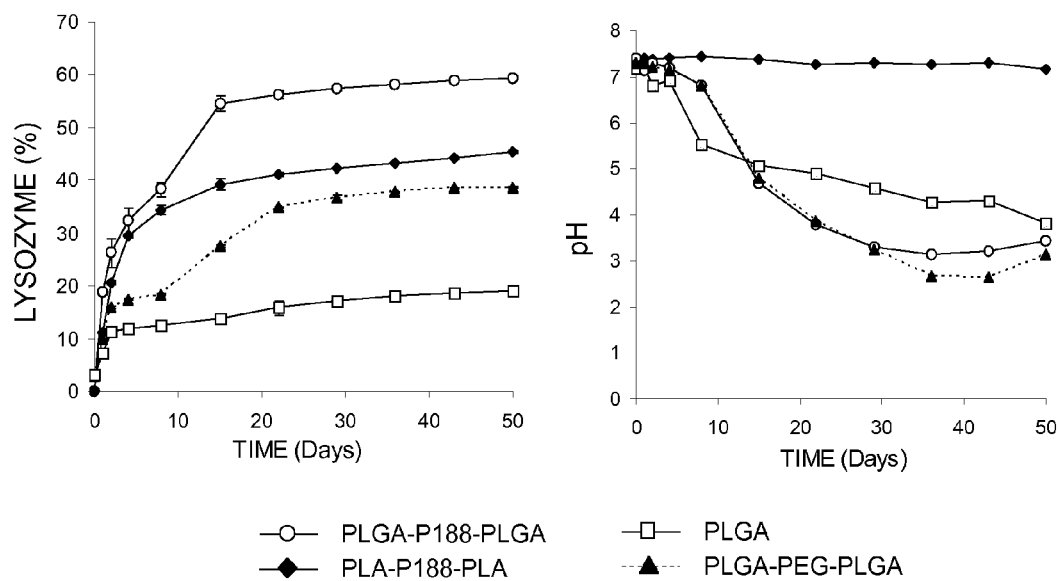
FIG. 6 shows in vitro lysozyme release from microspheres (A) and pH of the release medium buffer (B) 500 µl of Tris-HCl 0.05 M with 7 day interval removal.

FIG. 6 shows results of: (A) In vitro lysozyme release from microspheres (B) pH of the release medium buffer, 500 µl of Tris-HCl 0.05 M with 7 day interval removal.

45% of encapsulated lysozyme are released from the microspheres of PLA-P188-PLA copolymer against 38% for the PLGA-PEG-PLGA copolymer (Reference polymer). However, the majority of lysozyme from microspheres of PLA-P188-PLA (Polymer 3) was released during the first fifteen days. For the PLGA-P188-PLGA, 60% of lysozyme was released with a continuous release profile during the first 22 days.

Changes in the pH of the release medium is shown FIG. 6B. Unlike the acidic pH observed in the media release of PLGA, PLGA-PEG-PLGA and PLGA-P188-PLGA microspheres, the pH of the release medium of PLA-P188-PLA microspheres is always stable due to the slow degradation of PLA. In addition, the pH profiles of PLGA-PEG-PLGA and PLGA-P188-PLGA microspheres are similar. Exchanges between the indoor and outdoor microspheres and the rate of degradation of polymers could be close for both types of microspheres.

These results show clearly the interest of PLGA-P188-PLGA and PLA-P188-PLA to increase the percentage of protein release.

6. Amount of Encapsulated Active Lysozyme and In Vitro Evaluation of Active Lysozyme Release (Preparation 12)

Preparation 12

The tubes were incubated in a shaking water bath (37° C., 125 rpm). At determined time intervals, the tubes were centrifuged for 5 min at 2,800 g. 200 µL of the supernatant were collected for analysis and replaced by fresh buffer (250 µl). The percentage of biologically active released lysozyme was measured by enzymatic assay described in section 5.

Figure 7:
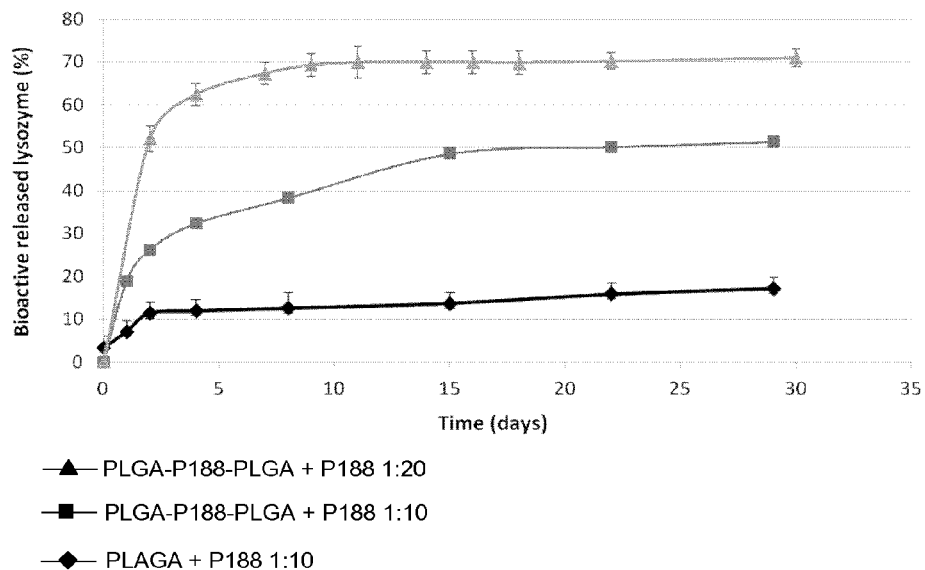
FIG. 7 is a graph illustrating the cumulative release of bioactive lysozyme from PLGA+P188 1:10, PLGA-P188-PLGA+P188 1:10, PLGA-P188-PLGA+P188 1:20 microspheres versus time.

Results are reported on FIG. 7 which shows the cumulative release of bioactive lysozyme from microspheres. PLGA+P188 1:10, PLGA-P188-PLGA+P188 1:10 PLGA-P188-PLGA+P188 1:20 were incubated in TRIS-HCL during 30 days at 37° C., and the lysozyme released at different time-points in the medium was measured with a bioassay. Each error bars represent the ±standard deviation of average percent cumulated values with n=3 for each formulation.

The impact of the polymer matrix (PLGA or PLGA-P188-PLGA) and the amount of P188 additive associated in the nanoprecipitation step with lysozyme on the release profile of bioactive lysozyme was evaluated and reported on FIG. 7.

i) The polymer matrix was modified with a fixed protein-P188 ratio of 1:10 for the nano-precipitation step. In these conditions, when PLGA-P188-PLGA was used as a matrix, the release of lysozyme from MS was significantly increased. At day 30, 51% of the encapsulated lysozyme was released compared to 17% for PLGA based MS. Indeed, at day 3, 12% of lysozyme was released from PLGA MS and low subsequent release was observed after this initial burst (from 12% to 17% at day 30). By contrast, when using PLGA-P188-PLGA as a matrix, the release was less pronounced, and a more sustained release was observed from day 0 to day 15, resulting in 51% of protein released at day 30.

Therefore, the use of a PLGA-P188-PLGA triblock copolymer significantly increases the release of lysozyme in comparison with PLGA compositions.

ii) Different ratios of poloxamer were then tested with PLGA-poloxamer-PLGA chosen as a polymer matrix.

Results: When Protein/poloxamer ratio was 1:20, the biologically active released protein was enhanced. As observed in FIG. 7, lysozyme release was increased from 51% at day 20 with Protein/poloxamer ratio 1:10 (as previously mentioned) to 71% when the protein-poloxamer ratio was 1:20.

Therefore, the use of lower Protein/poloxamer ratios significantly increases the release of lysozyme in comparison with higher ratios.

Moreover, a comparison between FIG. 7 and FIG. 6, shows that with the microspheres prepared with polymer 1 and 2 (PLGA-P188-PLAGA) at either a 0.6% or a 0.1% loaded protein percentage and a 1/10 protein/poloxamer ratio for both, the release profile is quite similar. In the first case near 55% of the protein is released at day 22 and 51% in the second case. It is therefore possible to considerably reduce the therapeutic protein loading by co-encapsulation of a carrier protein, such as albumin, nanoprecipitated separately and co-mixed with the therapeutic protein during the encapsulation step. This result is particularly interesting for expensive active pharmaceutical ingredients, particularly for therapeutic proteins.

7. Evaluation of Total TGF Beta 3 within the Microspheres and Coated Microspheres. Release Profile of Total and Bioactive TGF Beta 3 from Uncoated and Coated Microspheres To detect any loss in biological activity during the encapsulation process, the amount of active protein extracted from microspheres of example 3 was determined after dissolution of the microspheres in DMSO (5 mg/1 mL DMSO) (Bouffi 2010, §212) during 1 h (3 batches). After this time, samples were centrifuged and residual DMSO was evaporated. The encapsulated protein (such as TGF-β3) was measured using a specific ELISA kit (R&D Systems, Lille, France).

The encapsulation yield of TGF-β3 in PLGA microspheres was 116±22% and 89±12% in PLGA-P188-PLGA microspheres. The more hydrophilic properties of the triblock copolymer, reduce slightly the encapsulation yield. However, the encapsulation yield is satisfactory, the TGF-β3 loaded microspheres can be used to produce coated microspheres.

In Vitro Release of TGF-β3 from Microspheres

Microspheres constituted of either PLGA+P188 1:10, PLGA-P188-PLGA+P188 1:10, PLGA-P188-PLGA+P188 1:20 (preparation 13) were incubated in PBS 1% BSA, and the TGF-β3 released at different time-points in the medium was tested by ELISA (Duoset ELISA human TGF-β3 (R&D Systems, Lille, France) or bioassay described thereafter.

To assess the biological activity of TGF-β3 released from microspheres, a bioassay previously developed by Tesseur et al. (Highly sensitive and specific bioassay for measuring bioactive TGF-beta. BMC Cell Biol. 2006; 7:15,) was performed.

The bioassay relies on the use of mouse fibroblasts isolated from TGFβ1−/− mice (MFB-F11) stably transfected with a reporter plasmid consisting of TGF-β responsive Smad-binding elements coupled to the secreted alkaline phosphatase (SEAP) reporter gene. MFB-F11 fibroblasts were seeded at $3 \times 10^4$ cells/well in 96-well flat-bottom culture plates (Nunc®, Dutscher, France). After overnight incubation, cells were washed twice with phosphate buffer saline (PBS) and incubated in 50 μL serum-free DMEM supplemented with 100 U/mL penicillin and 100 mg/mL streptomycin (Lonza, Levallois-Perret, France).

After 2 h, 50 μL of TGF-β3 containing samples were added for another 24 h. Serial dilutions of determinate amounts of standard TGF-β3 were added to other wells to determine the standard curve. SEAP activity was measured on 50 μL of culture supernatants using the SEAP Reporter Gene Assay, chemiluminescent kit (Roche, Meylan, France) according to the manufacturer's instructions. Chemiluminescence was detected using a micro plate luminometer (Ascent FL, Thermo Fisher Scientific, Cergy-Pontoise, France) and the results were analyzed with the Ascent software for Fluoroscan (Thermo Fisher Scientific, Cergy-Pontoise, France).

Figure 8:
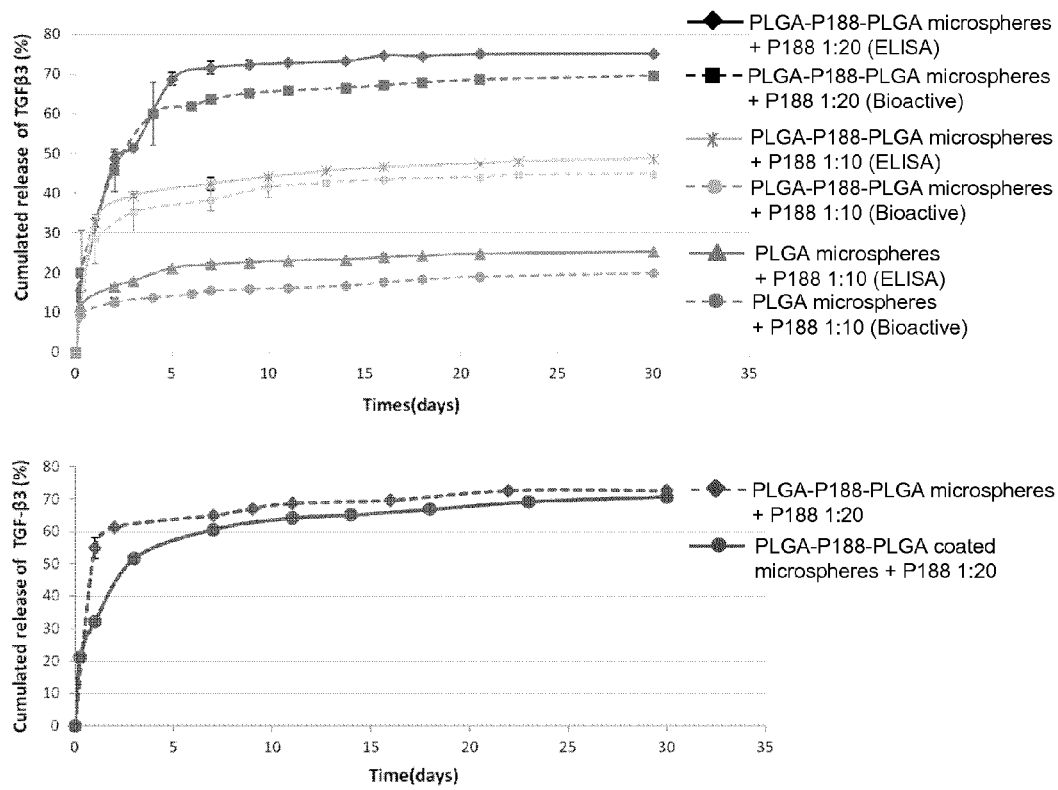
FIG. 8 is a graph illustrating the cumulative release of total and bioactive TGF-beta3 from microspheres constituted of either PLGA+P188 1:10, PLGA-P188-PLGA+P188 1:10 and PLGA-P188-PLGA+P188 1:20.

FIG. 8 shows the cumulative release of total and bioactive TGF-β3 from microspheres. A. Release profile of TGFB3, evaluated by ELISA and by a bioassay, from PLGA+P188 1:10, PLGA-P188-PLGA+P188 1:10, PLGA-P188-PLGA+ P188 1:20 (preparation 13) B. Comparison of release from PLGA-P188-PLGA (P188 1:20) microspheres (preparation 13) vs. coated microspheres loaded with TGF beta 3 (Preparation 13+preparation 10) Each error bar represents the ±standard deviation of average percent cumulated values with n=3 for each formulation.

Several microsphere formulations were tested:
PLGA microspheres encapsulating P188 nanoprecipitated with TGF-β3 at a TGF-β3:P188 ratio of 1:10 (w/w), PLGA-P188-PLGA microspheres+P188 1:10 and PLGA-P188-PLGA microspheres+P188 1:20 (FIG. 8A). A similar amount of TGF-β3 released from the microspheres was detected when measured by ELISA array or by a bioassay, indicating that the released TGF-β3 was bioactive. The release profiles of bioactive TGF-β3 were similar for each formulation with a higher initial release (day 0 to day 7) followed by a phase of slow release till day 30 (FIG. 8A).

These results show that the release profile of TGB3 when measured by ELISA matches the one measured with the bioassay. Therefore, TGFB3 released from all the different preparations is shown to be biologically active.

As observed for lysozyme, the release of TGF-β3 from PLGA microspheres was low, with 25% of TGF-β3 released at day 30, suggesting a degradation of the protein during release into the matrix.

The use of PLGA-P188-PLGA with a Protein/P188 ratio of 1:10 allowed a more pronounced release of TGF-β3 of around 40% from day 0 to day 3 followed by a weak release from day 3 to day 30 (10%).

Therefore, the use of a PLGA-P188-PLGA triblock copolymer significantly increases the release of lysozyme in comparison with PLGA compositions.

With the same matrix polymer (PLGA-P188-PLGA), and at a protein/P188 ratio of 1:20, 74% of bioactive TGF-β3 was released, with 60% released at day 6, and 14% between day 6 and day 30.

The mean value of bioactive TGF-β3 vs. the total released TGF-β3 ratio was around 56±8.9% for the PLGA formulation, whereas it was 96±12.5% for PLGA-P188-PLGA+ P188 1:20 formulations, suggesting a more efficient protein protection with this latter formulation.

Therefore, the use of lower Protein/P188 ratios significantly increases the release of TGF-β3 in comparison with higher ratios.

A comparison between TGF-β3 release from non-coated microspheres and FN-microspheres was performed with the aim to evaluate the influence of the coating on protein release (FIG. 8B)

The release from TGFB3 coated microspheres (preparation 13+preparation 10) was shown to be more sustained during 30 days compared to non-coated microspheres (preparation 13) (32% release at day 3 for microspheres of the invention vs. 55% released from non-coated microspheres), suggesting an influence of the coating step and the cell adhesion surface (fibronectin+poly D_lysine) in the protein release from the microspheres (FIG. 8B).

8. Chondrogenic Differentiation

Chondrogenic differentiation of hMSC with unloaded coated microspheres (Preparation 10) and coated microspheres releasing TGFB3 (Preparation 13+preparation 10) with a PLGA or PLGA-P188-PLGA matrix (polymer 2) was induced by 28 day culture in micropellets. Culture of hMSC with unloaded coated microspheres (preparation 10) and coated microspheres releasing TGFB (preparation 11) with a PLGA or PLGA-P188-PLGA matrix (polymer 2) were performed in micropellet in conical tube. Briefly, MSCs ($2.5 \times 10^5$ cells) and 0.5 mg coated microspheres were pelleted by centrifugation in 15 mL conical tubes, and cultured in chondrogenic medium. This medium consisted in DMEM supplemented with 0.1 mM dexamethasone, 0.17 mM ascorbic acid and 1% insulin transferrine selenic acid (ITS) supplement (Lonza). Standard chondrogenesis of MSCs was induced by culture in pellets in chondrogenic medium supplemented with 10 ng/mL TGF-B3. This served as comparison as it is the gold standard for chondrogenic differentiation in vitro by culture in micropellets.

Analysis: Quantitative qPCR

After 21 days of culture in micropellets, hMSCs with unloaded coated microspheres and coated microspheres releasing TGFβ3 with a PLGA or PLGA-P188-PLGA matrix were washed in PBS and mechanically dissociated in lysis buffer. Total RNA from cell preparations was then extracted, according to the recommendations of the manufacturer. Cells were lysed in a 1% β-mercaptoethanol containing buffer and RNA extracted following treatment by DNAse to remove any traces of genomic DNA (Total RNA isolation Nucleospin® RNA II, Macherey Nagel, Hoerdt, France). First strand cDNA synthesis was performed with SuperScript™ II Reverse Transcriptase (Invitrogen) according to the manufacturer's instructions. Following first strand cDNA synthesis, cDNAs were purified (Qiaquick PCR purification kit, Qiagen, Courtaboeuf, France), eluted in 50 µL RNAse free water (Gibco). cDNA (3.125 ng) were mixed with iQ SYBR Green Supermix (Biorad) and primer mix (0.2 mM) in a final volume of 10 µL. Amplification was carried on a Chromo4 thermocycler (Biorad) with a first denaturation step at 95° C. for 3 min and 40 cycles of 95° C. for 10 s, 55° C. for 15 s and 72° C. for 15 s. After amplification, a melting curve of the products determined the specificity of the primers for the targeted genes. A mean cycle threshold value (Ct) was obtained from 2 measurements for each cDNA. Several housekeeping genes, glyceraldehyde-3-phosphate dehydrogenase (Gapdh, NM_002046), beta 2 Microglobulin precursor (B2M, NM_004048), beta actin (Actb, NM_001101), and heat shock 90 kD protein 1 beta (Hspcb, NM_007355) were tested for normalization. The GeNorm® freeware (http://medgen.ugent.be/ejvdesomp/genorm/) was used to determine that Gapdh, Hprt1 & Hspcb were the three most stable housekeeping genes. The relative transcript quantity (Q) was determined by the delta cT method [Q=E (Ct min in all the samples tested-Ct of the sample)] where E is related to the primer efficiency (E=2 if the primer efficiency=100%). Relative quantities (Q) were normalized using the multiple normalization method described in Vandesompele et al. [29].

Figure 9:
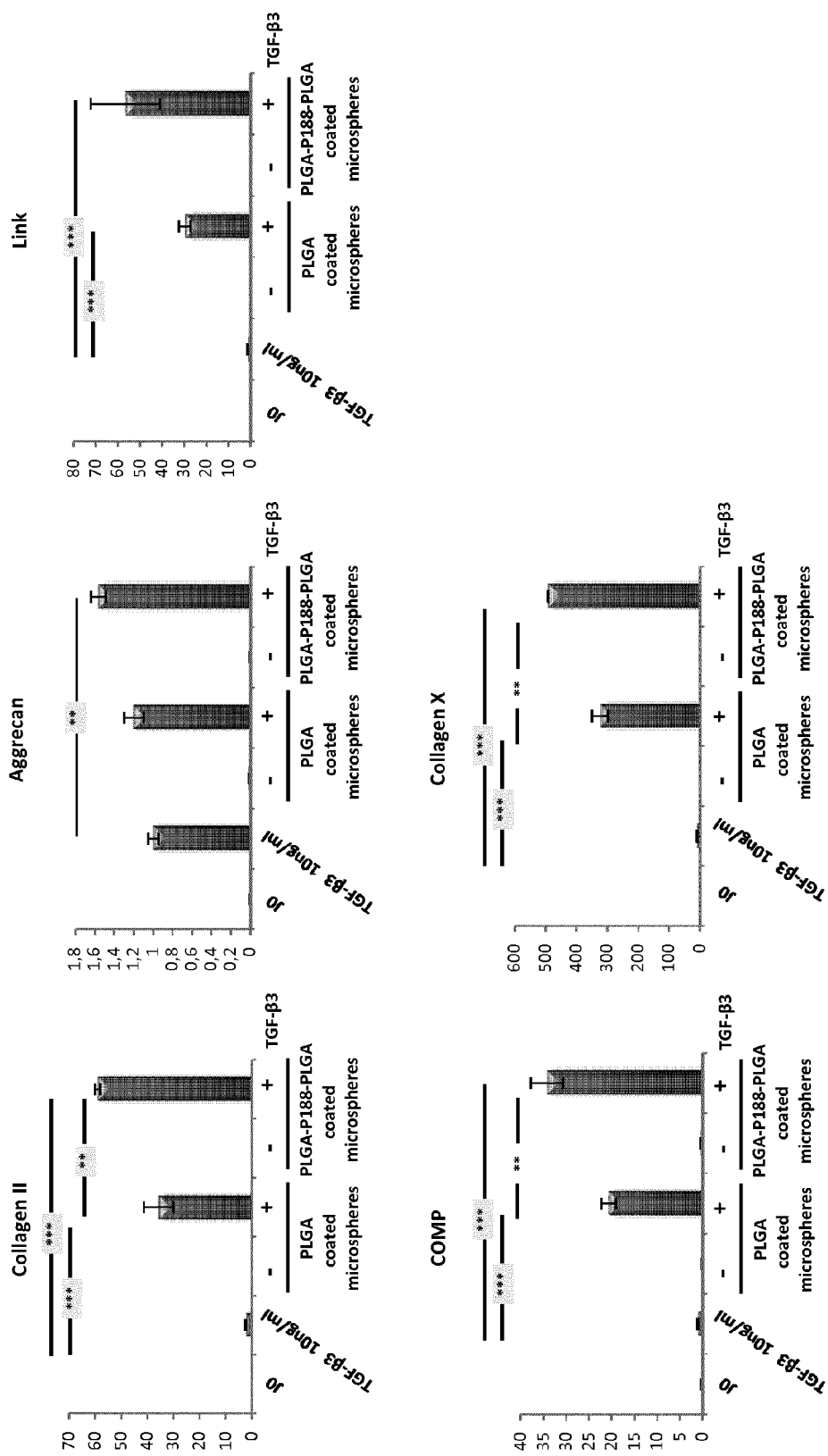
FIG. 9 shows chondrogenic differentiation of hMSCs cultured in vitro with PLGA coated microspheres or PLGA-P188-PLGA coated microspheres releasing or not TGFb3. Expression of chondrocytes markers (A), adypogenic markers (B) and osteogenic marker (C).

FIG. 9 illustrates the chondrogenic differentiation of hMSCs cultured in vitro with PLGA coated microspheres or PLGA-P188-PLGA coated microspheres releasing or not TGFb3. Expression of chondrocytes markers (A), adypogenic markers (B) and osteogenic marker (C).

By RT-qPCR analysis the increased expression of all the tested chondrogenic markers (collagen II B variant, link, aggrecan, COMP) by MSCs cultured with TGF-β3 releasing coated microspheres compared to the gold standard for chondrogenic differentiation is observed in vitro (FIG. 9). Moreover, differences can be observed between the two coated microsphere formulations, with a significant up-regulation in the expression of collagen 2 and COMP when hMSC were associated to the new formulation composed of PLGA-P1288-PLGA matrix (from 35 to 59 fold increased expression of collagen 2 for TGF-β3 PLGA coated microspheres vs. TGF-β3 PLGA-P188-PLGA coated microspheres respectively). Of note, no chondrogenic markers were detected when cells were cultured with unloaded PLGA-P188-PLGA coated microspheres. These results suggest an induction of chondrogenic differentiation by the continuous release of TGF-β3 by FN-coated microspheres. It is important to note that, in our study, the osteogenic markers, AP and osteocalcin, were expressed at low levels whatever were the conditions compared to non-treated cells at D0 (FIG. 9). Interestingly, compared to cells without treatment (D0), in all the other conditions, the adypocytic markers were down regulated, except for unloaded FN PLGA-P188-PLGA coated microspheres (FIG. 9). This strongly suggests the importance of the released growth factor for an efficient and specific chondrogenic differentiation, as well as the influence of the matrix properties.

Analysis: Histology and Immunohistochemistry

After 21 days of culture in micropellets, hMSCs with unloaded coated microspheres and coated microspheres releasing TGFB were fixed in 4% paraformaldehyde for 24 h, washed in PBS and processed for routine histology. Paraffin-embedded samples sections (5 mm) were rehydrated through a gradient of ethanol and xylene and stained with hematoxylin-eosin.

Immunohistochemistry was performed on sample sections using the Ultravision detection system anti polyvalent HRP/DABkit (LabVision, Microm, Francheville, France), according to the manufacturer's instructions.

For type II collagen and aggrecan immunostaining, the micropellets of hMSCs with unloaded coated microspheres and coated microspheres releasing TGF beta 3 were first incubated at 37° C. for 1 h with hyaluronidase 0.1% (Sigma) for epitope retrieval. Primary antibodies, anti aggrecan polyclonal rabbit antibody (1:50; Millipore, Molsheim, France) or anti-type II collagen monoclonal mouse antibody (1:50; Interchim) were incubated for 1 h at RT with the micropellets of hMSCs with unloaded coated microspheres and coated microspheres releasing TGF beta. They were then finally counterstained with Mayer's hematoxylin (LabVision) for 3 min and mounted with Eukitt (Sigma). Immunopositive extracellular matrix showed a brown staining.

hMSC were cultured in micropellets with TGF-β3 PLGA coated microspheres (A, D), TGF-β3 PLGA-P188-PLGA coated microspheres (B, E) unloaded PLGA-P188-PLGA coated microspheres (C, F). Thus-formed complexes were embedded in paraffin section after day 28 to allow immunostaining.

A, B and C represent immunostaining for collagen II whereas D, E, F are immunostaining for aggrecan.

Figure 10:
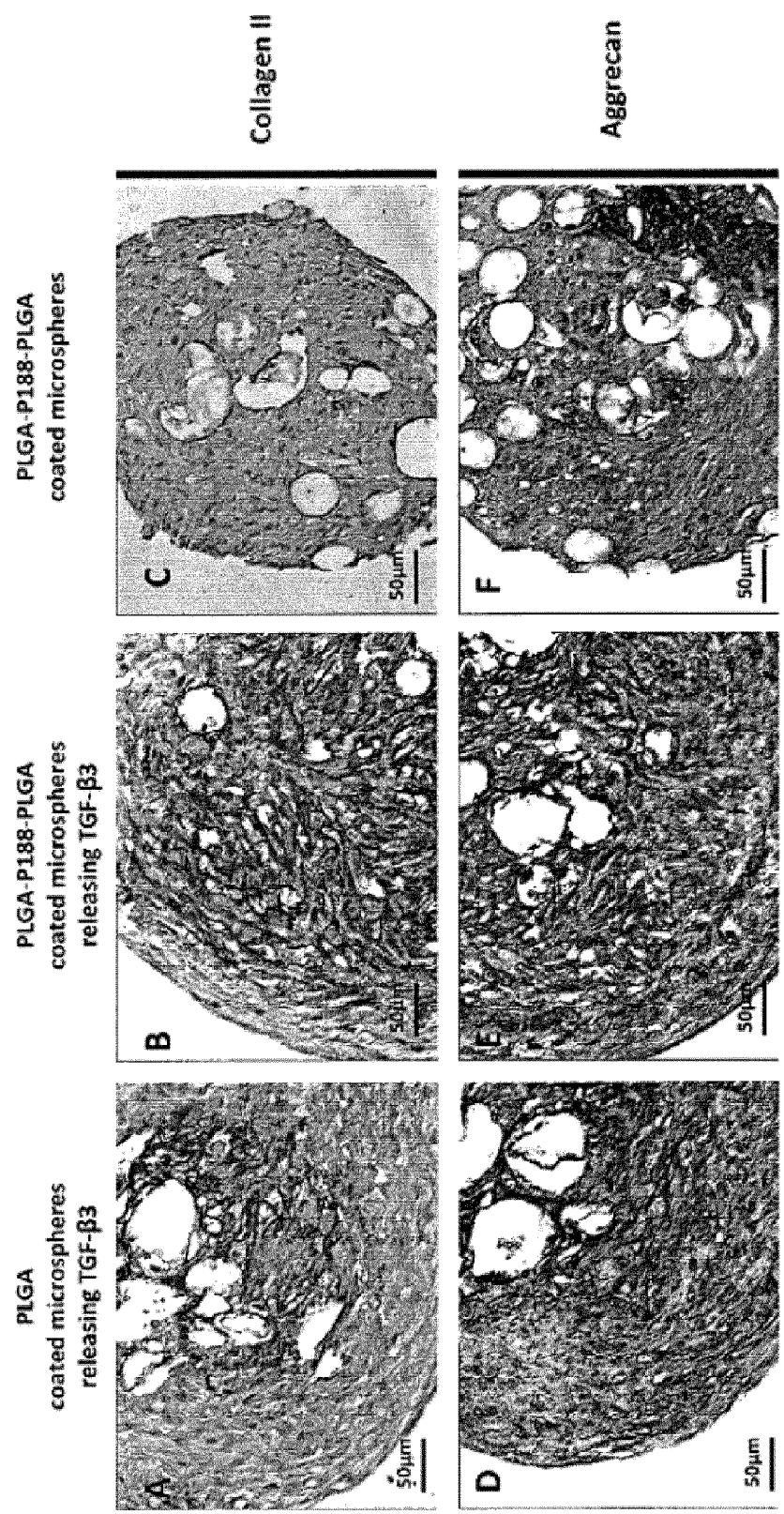
FIG. 10 is a picture showing the immunostaining of collagen II (A, B, C) and aggrecan (D, E, F), components of the cartilaginous extracellular matrix, when hMSC were cultured for 28 days in micropellets with unloaded Coated microspheres (A, D) TGFb3-Coated microspheres PLGA (B, E) and TGFb3 coated microspheres PLGA-P188-PLGA (C, F).

Results are reported on FIG. 10 which shows the expression of cartilage ECM molecules.

The immunohistochemical specific staining for type II collagen (FIG. 10 A, B, C) showed an intense staining evenly distributed especially when hMSC were associated to FN-PLGA-P188-PLGA coated microspheres releasing TGFB3 (FIG. 10 C). The staining intensity was weaker with FN PLGA coated microspheres and no specific type II collagen expression was seen for unloaded PLGA-P188-PLGA coated microspheres. By contrast, aggrecan staining can be observed when cells are associated with unloaded PLGA-P188-PLGA coated microspheres (in agreement with the expression of this protein at a basal level in hMSC) (FIG. 10 D). Nevertheless, this staining was more intense when cells were cultured with coated microspheres releasing TGF-β3 (FIG. 10 E, F).

These results evidence that coated microspheres releasing TGFB3 induce chondrogenic differentiation of hMSC which secrete cartilage ECM molecules. Moreover FN-PLGA-P188-PLGA coated microspheres releasing TGFB3 better stimulate the chondrogenic differentiation of the cells probably due to the increased release profile.

What is claimed is:

1. A cell carrying microsphere composition, wherein the microsphere composition consists of:

a microspheric core comprising a copolymer matrix A-B-A, wherein A is poly(lactide-co-glycolide) (PLGA) or polylactide (PLA) and B is a poloxamer or a poloxamine, wherein the microspheric core is coated with a cell adhesion coating, whole cells or cell fragments bound to the cell adhesion coating, and optionally, an active ingredient embedded within the microspheric core.

2. The cell carrying microsphere composition according to claim 1, wherein A is PLGA.

3. The cell carrying microsphere composition according to claim 1, wherein B is a poloxamer.

4. The cell carrying microsphere composition according to claim 1, wherein the proportion of poloxamer or poloxamine in the copolymer matrix A-B-A is between 2 and 40% (w/w).

5. The cell carrying microsphere composition according to claim 1, comprising whole cells.

6. The cell carrying microsphere composition according to claim 1, wherein the active ingredient is a protein.

7. The cell carrying microsphere composition according to claim 1, wherein the cell adhesion coating comprises fibronectin and poly-D-lysine.

8. A process for the preparation of a cell carrying microsphere of claim 1 consisting of the steps of:

providing microspheric cores comprising a copolymer matrix A-B-A wherein A is PLGA or PLA and B is a poloxamer or a poloxamine, fully or partly coating the microspheres with a cell adhesion compound, and contacting whole cells or cell fragments with the microspheres presenting the cell adhesion surface, for obtaining a cell carrying microsphere composition comprising whole cells or cell fragments; and optionally, prior to fully or partly coating the microspheres with a cell adhesion compound:

providing an active ingredient, adding the active ingredient in the solution of the A-B-A copolymer matrix, emulsifying or suspending, emulsifying the solution of A-B-A copolymer matrix in an aqueous phase containing a surfactant, removing the solvent of polymers, whereby obtaining microspheres forming a matrix wherein the active ingredient is embedded, and isolating the microspheres.

9. A method for therapeutic treatment of the human or animal body comprising a step of administering to a human or an animal a therapeutically effective amount of a cell carrying microsphere composition as defined in claim 1.

10. A method for therapeutic treatment of degenerative diseases in a subject comprising a step of administering to the subject a therapeutically effective amount of cell carrying microsphere composition as defined in claim 1 comprising whole cells or cell active fragments active for treating degenerative diseases.

11. A pharmaceutical composition comprising a cell carrying microsphere composition as defined in claim 1 at least one pharmaceutically acceptable carrier, and at least one therapeutic and/or prophylactic ingredient.

* * * * *